(12) United States Patent
Manak et al.

(10) Patent No.: US 8,038,347 B2
(45) Date of Patent: Oct. 18, 2011

(54) PORTABLE TOMOGRAPHIC DIAGNOSTIC SYSTEM WITH OPEN GANTRY

(75) Inventors: Joseph John Manak, Albany, NY (US); David Allen Langan, Clifton Park, NY (US); Bernhard Erich Hermann Claus, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 930 days.

(21) Appl. No.: 11/962,660

(22) Filed: Dec. 21, 2007

(65) Prior Publication Data

US 2010/0310044 A1    Dec. 9, 2010

(51) Int. Cl.
*H05G 1/60* (2006.01)
*H05G 1/64* (2006.01)
*A61B 6/04* (2006.01)

(52) U.S. Cl. ........ 378/189; 378/196; 378/197; 378/198; 378/209; 5/601

(58) Field of Classification Search .................. 378/124, 378/134, 189, 196, 197, 198, 209; 5/601; 250/370.09
See application file for complete search history.

(56) References Cited

U.S. PATENT DOCUMENTS

| | | | |
|---|---|---|---|
| 4,181,347 A * | 1/1980 | Clark | 378/199 |
| 4,349,740 A * | 9/1982 | Grassmann et al. | 378/25 |
| 5,048,070 A * | 9/1991 | Maehama et al. | 378/197 |
| 5,117,446 A * | 5/1992 | Haaker et al. | 378/98.3 |
| 5,142,652 A * | 8/1992 | Reichenberger et al. | 378/136 |
| 5,222,115 A * | 6/1993 | Highgenboten | 378/177 |
| 5,422,928 A * | 6/1995 | Payne | 378/177 |
| 5,511,105 A * | 4/1996 | Knott | 378/134 |
| 5,525,905 A * | 6/1996 | Mohapatra et al. | 324/318 |
| 5,572,567 A * | 11/1996 | Khutoryansky et al. | 378/197 |
| 5,661,309 A * | 8/1997 | Jeromin et al. | 250/580 |
| 5,877,501 A * | 3/1999 | Ivan et al. | 250/370.09 |
| 6,215,848 B1 * | 4/2001 | Linders et al. | 378/98.12 |
| 6,266,831 B1 * | 7/2001 | Heimbrock | 5/601 |
| 6,292,534 B1 * | 9/2001 | Linders et al. | 378/98.12 |
| 6,341,156 B1 * | 1/2002 | Baetz et al. | 378/98.8 |
| 6,398,409 B1 * | 6/2002 | Brooks | 378/209 |
| 6,481,887 B1 * | 11/2002 | Mirabella | 378/198 |
| 6,604,855 B2 * | 8/2003 | Katoh et al. | 378/196 |
| 6,632,019 B2 * | 10/2003 | Katoh | 378/197 |
| 6,672,760 B2 * | 1/2004 | Ishii et al. | 378/198 |
| 6,926,441 B2 * | 8/2005 | Stout, Jr. | 378/177 |
| 6,934,361 B2 * | 8/2005 | Ohkoda | 378/98.8 |
| 7,015,478 B2 * | 3/2006 | Yamamoto | 250/370.09 |
| 7,104,686 B2 * | 9/2006 | Watanabe et al. | 378/189 |
| 7,478,947 B2 * | 1/2009 | Kobayashi | 378/181 |
| 2004/0264649 A1 * | 12/2004 | Jahrling | 378/209 |

* cited by examiner

*Primary Examiner* — Allen C. Ho
(74) *Attorney, Agent, or Firm* — Jason K. Klindtworth

(57) ABSTRACT

An imaging system includes a portable litter including a structural housing and a digital detector positioned in the structural housing to detect X-ray signals corresponding to a region of interest to be imaged. The imaging system further includes at least one X-ray source for generating the X-ray signals, the at least one X-ray source positioned above the portable litter on an open gantry arrangement and configured to generate X-rays from different focal spot locations.

27 Claims, 6 Drawing Sheets

US 8,038,347 B2

PORTABLE TOMOGRAPHIC DIAGNOSTIC SYSTEM WITH OPEN GANTRY

STATEMENT REGARDING FEDERALLY SPONSORED RESEARCH & DEVELOPMENT

This invention was made with Government support under contract number W81XWH-05-C-0065 awarded by the Defense Advanced Research Projects Agency. The Government has certain rights in the invention.

BACKGROUND

Embodiments of the invention relate generally to the field of non-invasive imaging, including medical imaging.

Imaging plays a pivotal role in today's trauma assessment and intervention. Imaging is used for injury assessment in cases where the patient's condition is not immediately life threatening and where the extent of an injury is uncertain. In a hospital setting, ultrasound and X-ray radiography are widely available and commonly employed. However, despite the imaging advantages of X-ray fluoroscopy or computed tomography (CT), their use in assessment is limited by several factors including equipment availability, patient transport and delay. For example, transport and set-up of CT or X-ray C-arm systems is challenging due to the equipments size, weight, and fragility of moving parts. High-speed gantry rotations required for 3D imaging require facilities support for safe reliable operation that is not always available. In providing trauma assessment and care in military far forward settings, for example, imaging systems should be easily transportable with few to no high speed moving parts.

BRIEF DESCRIPTION

In accordance with one aspect of the invention, a portable litter for imaging includes a structural housing, a digital detector positioned in the structural housing to detect X-ray signals corresponding to a region of interest to be imaged, a radiolucent surface disposed above the digital detector, and an energy storage device coupled to the digital detector.

In accordance with another aspect of the invention, an imaging system includes a portable litter including a structural housing and a digital detector positioned in the structural housing to detect X-ray signals corresponding to a region of interest to be imaged. The imaging system further includes at least one X-ray source for generating the X-ray signals, the at least one X-ray source positioned above the portable litter on an open gantry arrangement and configured to generate X-rays from different focal spot locations.

In accordance with a further aspect of the invention, a patient transport for imaging is described. The patient transport includes a cab, and a cargo area attached to the cab. The cargo area includes a ceiling and a floor with an open gantry arrangement fixedly coupled to the ceiling with an X-ray source for generating X-ray signals coupled to the open gantry arrangement. The cargo area further includes a support structure coupled to the floor of the cargo area, and a portable litter removably coupled to the support structure. The portable litter includes a structural housing and a digital detector coupled to the structural housing to detect X-ray signals from the source.

In yet a further aspect of the invention, an X-ray detection kit is provided. The X-ray detection kit includes an X-ray detector system including a plurality of attachment sites configured to detachably couple the X-ray detector system to a portable litter to facilitate image acquisition. The X-ray detector system further includes a digital detector to detect X-ray signals corresponding to a region of interest to be imaged, an energy storage device electrically coupled to the digital detector, readout circuitry to determine an X-ray exposure state of picture elements within the digital detector, and a communications interface to provide data communication between the X-ray detector system and a processor for processing image acquisition information.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

In accordance with various embodiments, a portable tomographic diagnostic system including an open gantry and portable litter adapted for imaging are described. In the following detailed description, numerous specific details are set forth in order to provide a thorough understanding of various embodiments of the present invention. However, those skilled in the art will understand that embodiments of the present invention may be practiced without these specific details, that the present invention is not limited to the depicted embodiments, and that the present invention may be practiced in a variety of alternative embodiments. In other instances, well known methods, procedures, and components have not been described in detail.

Furthermore, various operations may be described as multiple discrete steps performed in a manner that is helpful for understanding embodiments of the present invention. However, the order of description should not be construed as to imply that these operations need be performed in the order they are presented, nor that they are even order dependent. Moreover, repeated usage of the phrase "in one embodiment" does not necessarily refer to the same embodiment, although it may. Lastly, the terms "comprising", "including", "having", and the like, as well as their inflected forms as used in the present application, are intended to be synonymous unless otherwise indicated.

In accordance with one aspect of the invention, a portable litter is uniquely adapted to not only transport subjects that may be injured or incapacitated from one location to another, but also to function as a detector for diagnostic imaging of the subject. As will be described in further detail, by integrating image detection components directly into the portable litter, subjects may be positioned near an imaging source such as an X-ray emitter, and imaged to assess a level of trauma or to perform an interventional procedure without having to be moved or transferred from the litter. In accordance with another aspect of the invention, the portable litter for imaging may be used in conjunction with a patient transport having at least one X-ray source positioned on an open gantry arrangement integrated with the transport. The combination of a portable open source gantry and a portable litter adapted for imaging allows local and remote caregivers and first responders the ability to quickly assess the condition of a subject, and to provide interventional procedures if necessary without the need to move the subject and risk additional injury.

Figure 1:
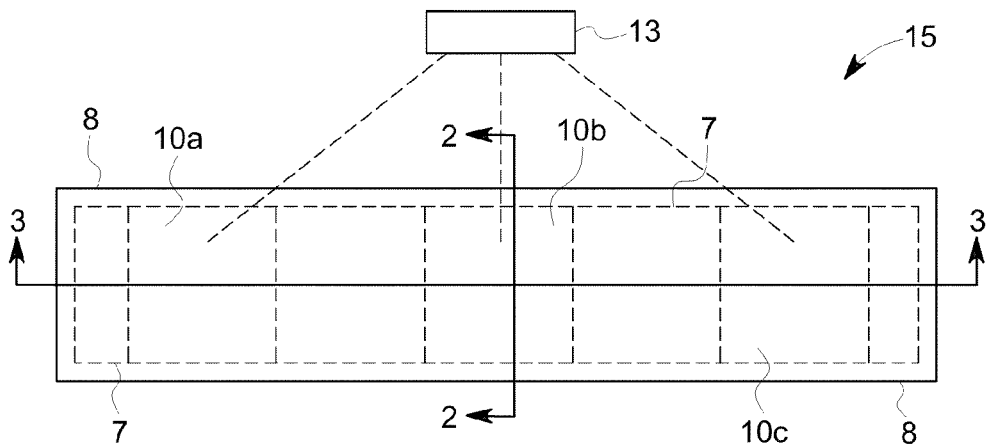
FIGS. 1-3 illustrate varying views of a portable litter for imaging in accordance with one embodiment of the invention.
Figure 2:
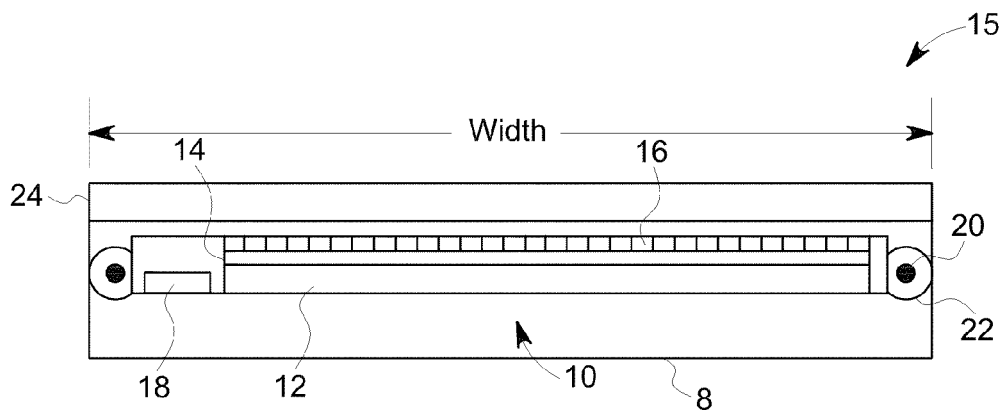
Figure 3:
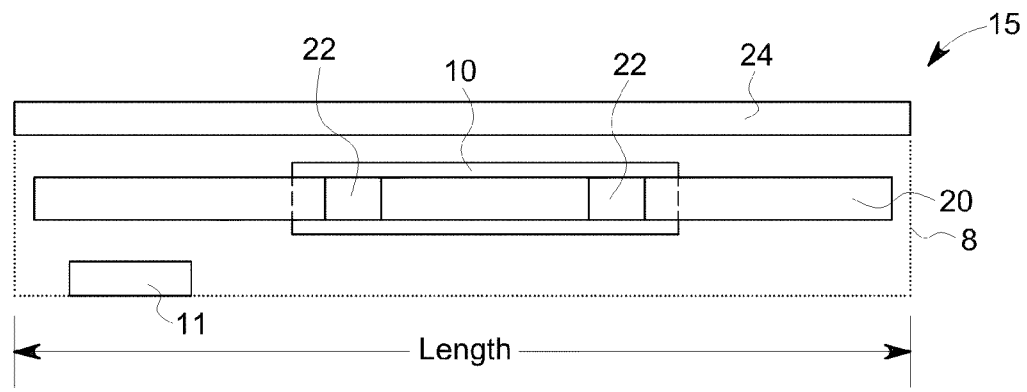

FIGS. 1-3 illustrate varying views of a portable litter for imaging in accordance with one embodiment of the invention. As shown, portable litter 15 includes a structural housing 8, one or more digital detectors 10, an energy storage device 11 coupled to the digital detector 10, and a radiolucent surface 24 disposed over the digital detector 10.

The structural housing 8 represents a substantially rigid frame configured to support the weight and body types of a wide range of subjects. In the illustrated embodiment, the structural housing 8 is shown as being substantially rectilinear, however, the housing, and more generally the portable litters described herein, may be structured with a variety of form factors and contours without departing from the spirit and scope of the invention. In various embodiments, the structural housing 8 may be formed from one or more metals or composite materials. More specifically, the structural housing 8 may be manufactured from radio opaque materials such as aluminum, stainless steel, and titanium, or from radiolucent materials such as thermoplastics and carbon fiber, or from a combination of radiolucent and radio opaque materials. The structural housing 8 may be molded as a unitary housing or assembled from multiple sub-components. Moreover, the structural housing 8 may include one or more cross-members to provide additional rigidity. Furthermore, structural housing 8 may include one or more sets of handles or holds to facilitate lift and transport by two or more people.

In one embodiment, at least one digital detector 10 is positioned in the structural housing to detect X-ray signals corresponding to a region of interest to be imaged on a subject. In one embodiment, the digital detector 10 is a substantially flat panel detector. In another embodiment, the detector may be curved, or may have a complex shape including one or more contours. In one embodiment, the digital detector 10 may represent an energy integrating detector that performs indirect or direct energy conversion. However, in other embodiments, the digital detector 10 may represent photon counting detectors and energy discriminating detectors that perform direct or indirect energy conversion.

In one embodiment, the digital detector 10 may include an energy conversion layer 16, an electronics layer 14, and a substrate 12. The substrate 12 provides structural support to the panel and may be formed from glass for example. The energy conversion layer 16 absorbs X-ray photons and converts their energy into visible light emission. In one embodiment, the energy conversion layer 16 comprises a cesium iodide (CsI) scintillator. The electronics layer 14 may represent an amorphous silicon photodiode array and thin-film transistors (TFTs). The photodiode array and thin-film transistors (TFTs) may be formed directly on the substrate 12. In operation, each photodiode represents a picture element and the charge of each photodiode is depleted in proportion to the amount of light the photodiode receives. In turn, the thin-film transistors are used to gate the output from the photodiodes which is then read by readout circuitry 18. The readout circuitry 18 is coupled to the digital detector 10 to determine an X-ray exposure state of the picture elements within the detector. In one embodiment, the readout circuitry measures the charge of the corresponding photo-diode through a matrix column and converts the charge measure to a digital value through an analog to digital converter attached to each column In certain embodiments, the digital detector 10 may also include an anti-scatter grid to reduce X-ray scatter.

In an embodiment where more than one detector is used, the detectors may be spaced apart and selectively coupled to an image processor 13 based upon the location of the region of interest to be imaged. For example, as illustrated in FIG. 1, a portable litter for imaging may include a first digital detector 10 positioned near an end of the structural housing 8 where a subject's head may typically be located (e.g., position 10a), a second digital detector 10 positioned where a torso might normally be located (e.g., position 10b), and a third digital detector 10 positioned where a subject's lower body may be located (e.g., position 10c). Each such digital detector may be selectively coupled or decoupled to an imaging system 13 e.g., through a multiplexer or other switching logic or if sufficient resources are available the detectors may each be operated in parallel.

The detectors may be fixed in a particular location or they may be adjustable. In one embodiment, one or more detectors may be slidably coupled to the structural housing 8 and movable in a longitudinal direction (e.g., along the length), a lateral direction (across the width), or both longitudinal and lateral directions. For example, in FIG. 1, dotted reference area 7 may represent the range of longitudinal movement capable by a digital detector 10 within the portable litter 15.

In one embodiment, the digital detector 10 may be slidably coupled using two or more supports 20, such as rails, tracks or brackets, as shown in FIG. 2 and FIG. 3. In the illustrated embodiment, the supports 20 are coupled to the structural housing 8 at or near two opposing ends of the housing. The supports 20 may have a cross-section that is round, flat, hemispherical, or other shape so as to facilitate sliding of the digital detector 10 along the length, width or length and width of the portable litter 15. In one embodiment, the digital detector 10 may slide along the supports 20 using collars 22 secured to the detector. The collars are not limited to any particular form or cross-section but function as bearings (e.g., fluid, air, ball, etc . . . ) to facilitate relative motion between the digital detector 10 and the structural housing. In the illustrated embodiment, the collars 22 are laterally secured to the digital detector 10 such that the detector is mounted substantially between the supports 20. In one embodiment, the digital detector 10 may be secured in any desired location along the supports using a locking mechanism. Further, the digital detector 10 may be positioned manually by an operator or automatically, e.g. through a servomotor. Additionally, the digital detector may be moved between X-ray exposures and the resulting image acquisition data can be electronically stitched together to facilitate larger anatomical coverage.

The portable litter 15 further includes an energy storage device 11 for providing operating current to the digital detector 10 and other electronic components within the portable litter. The energy storage device 11 may represent a variety of energy storage devices such as one or more batteries, capacitors, inductors, or a combination thereof. The energy storage device 11 may be rechargeable and the portable litter 15 may include the option of being plugged in to a power distribution network when one is available. Furthermore, the portable litter 15 may include a standby mode where the digital detector operates in a low power mode until it is time to image at which point a higher power mode may be activated. By keeping the detector in a low power mode, detector initialization time may be decreased thereby providing for earlier imaging.

The portable litter 15 further includes a radiolucent surface 24 coupled to the structural housing 8 and disposed over the digital detector 10. The radiolucent surface 24 may be formed from a wide variety of radiolucent materials to provide lateral support to a subject to be imaged while not interfering with X-rays emitted from a source. The radiolucent surface may be rigid, semi-rigid or compliant, and the surface may appear as a solid or a woven mesh, for example.

In one embodiment, the digital detector 10 may be packaged as an X-ray detection kit. The X-ray detection kit may include an X-ray detection system including one or more attachment sites configured to detachably couple the X-ray detector system to a portable litter such as the portable litter 15 to facilitate image acquisition. The attachment sites may be configured to clamp, bolt, screw, tie or otherwise interface with a support structure such as, for example, the supports 20 or 30 described herein. In one embodiment, the attachment sites may include one or more collars such as collars 22 or 32 as described herein. The X-ray detector system may include a digital detector (e.g., digital detector 10) to detect X-ray signals corresponding to a region of interest to be imaged, an energy storage device (e.g., energy storage device 11) electrically coupled to the digital detector and readout circuitry (e.g., readout circuitry 18) to determine an X-ray exposure state of picture elements within the digital detector. The X-ray detector system may further include a communications interface to provide data communication between the X-ray detector system and a processor (not shown) for processing image acquisition information. The digital detector system components and any associated interconnections may further be integrated into a unitary housing to facilitate quick and easy attachment and removal from the portable litter.

Figure 4:
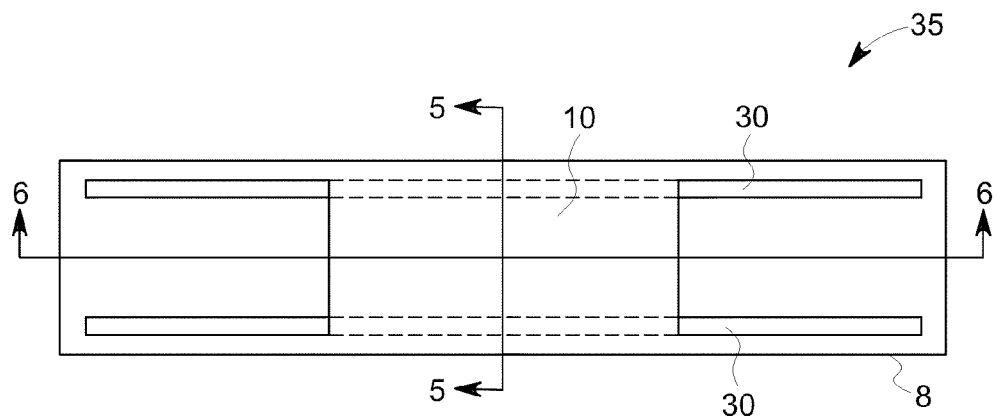
FIGS. 4-6 illustrate varying views of a portable litter for imaging in accordance with an alternative embodiment of the invention.
Figure 5:
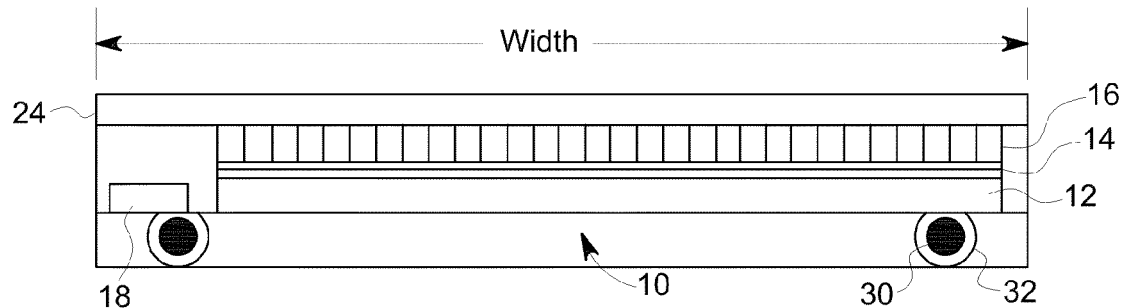
Figure 6:
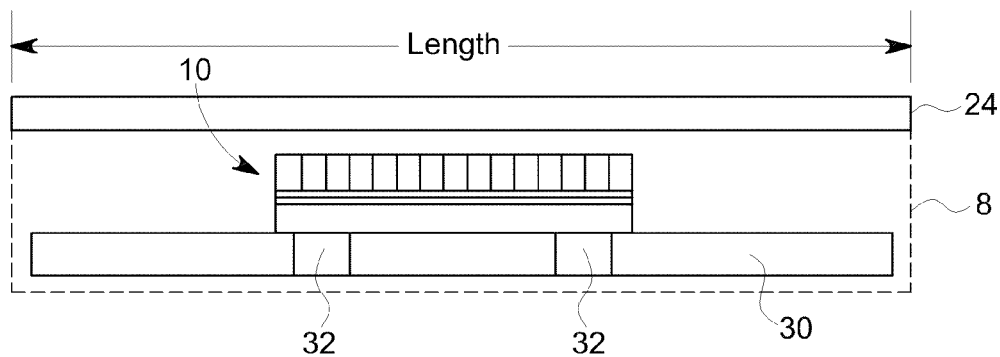

FIGS. 4-6 illustrate varying views of a portable litter 35 for imaging in accordance with an alternative embodiment of the invention. The portable litter 35 is substantially similar to portable litter 15 of FIGS. 1-3, however portable litter 35 is mounted above supports 30. More specifically, in FIGS. 4-6, the digital detector 10 is slidably coupled to the supports 30 by collars 32 that are mounted to the underside (e.g., opposite the imaging surface) of the detectors. Accordingly, the digital detector 10 can be made wider or allowed to travel further in a lateral direction than the embodiment illustrated in FIGS. 1-3. Although not illustrated, the digital detector 10 may nonetheless be coupled to more than two supports or a single support without departing from the spirit and scope of the invention.

Figure 7:
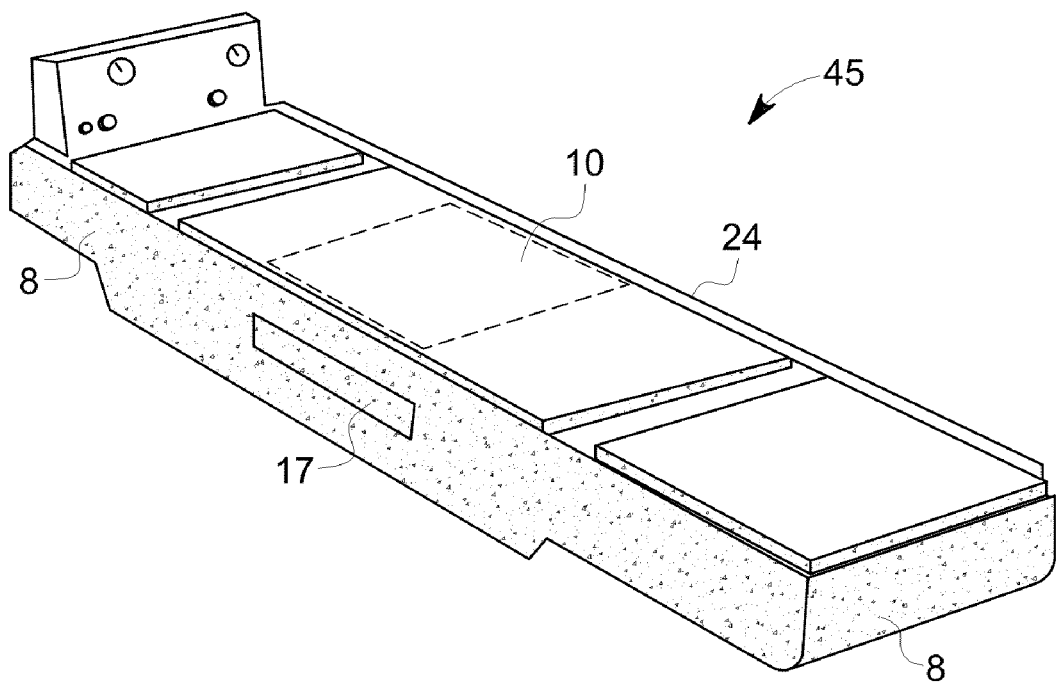
FIG. 7 illustrates a perspective view of a portable litter for imaging in accordance with one embodiment of the invention.

FIG. 7 illustrates a perspective view of a portable litter 45 for imaging in accordance with one embodiment of the invention. In the illustrated embodiment, portable litter 45 includes a structural housing 8, a digital detector 10 (shown in phantom) coupled within the structural housing 8 and a radiolucent surface 24 disposed over the detector. In one embodiment, the structural housing 8 may further include at least one monitoring device 17 for monitoring at least one physiological measurement of a subject. The monitoring device 17 may be electrically coupled to the energy source 11 and may include functionality such as an EKG machine, blood pressure monitor, blood oxygen detector, pulse monitor, thermometer, and a blood sugar detector. In one embodiment, X-ray acquisitions may be gated based upon one or more physiological measurements of a subject. For example, the X-ray acquisitions may be gated based upon heart phase and/or respiratory phase to reduce motion blurring in reconstructed images.

In accordance with another aspect of the invention, a portable imaging system is provided. The portable imaging system may include a portable litter and at least one X-ray source for generating the X-ray signals. The portable litter may include a structural housing and a digital detector positioned in the structural housing to detect X-ray signals corresponding to a region of interest to be imaged. The one or more X-ray sources may be positioned above the portable litter on an open gantry arrangement and configured to generate X-rays from different focal spot locations.

Figure 8A:
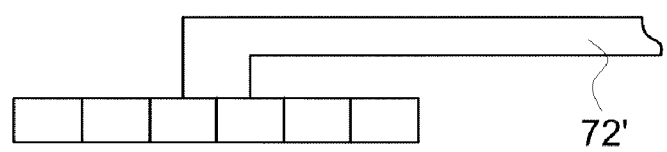
FIG. 8A and 8B are schematic views illustrating imaging systems in accordance with other aspect of the invention.

The portable imaging system described herein may include one or more single X-ray sources or one or more distributed X-ray sources (each comprising multiple focal spots), or a combination thereof. Similarly, the one or more X-ray sources may include a single vacuum tube or multiple vacuum tubes and may have a single X-ray emitter or multiple discrete X-ray emitters. In one embodiment shown in FIG. 8A, a distributed X-ray source comprising a one-dimensional or two-dimensional array of X-ray focal spots may be mounted on a gantry 72'. The X-ray focal spots in the array may be located in the same plane or in different planes. Moreover, the array of X-ray focal spots may be substantially linear or they may form an arcuate configuration. In one embodiment, one or more of the (single or distributed) X-ray source may be moved on an open gantry in one or more directions to generate X-rays at multiple focal spot locations. In another embodiment, X-ray image acquisitions with varying focal spot positions are achieved by simply activating different focal spots on a distributed X-ray source. IN an alternative embodiment, a portable litter including a digital detector as described herein may be moved with respect to the one or more X-ray sources such that X-rays are generated at multiple focal spot locations relative to the imaged anatomy. IN various embodiments, the one or more X-ray sources may also include one or more collimators to further direct or focus the generated X-rays.

Figure 8A:
Figure 8B:
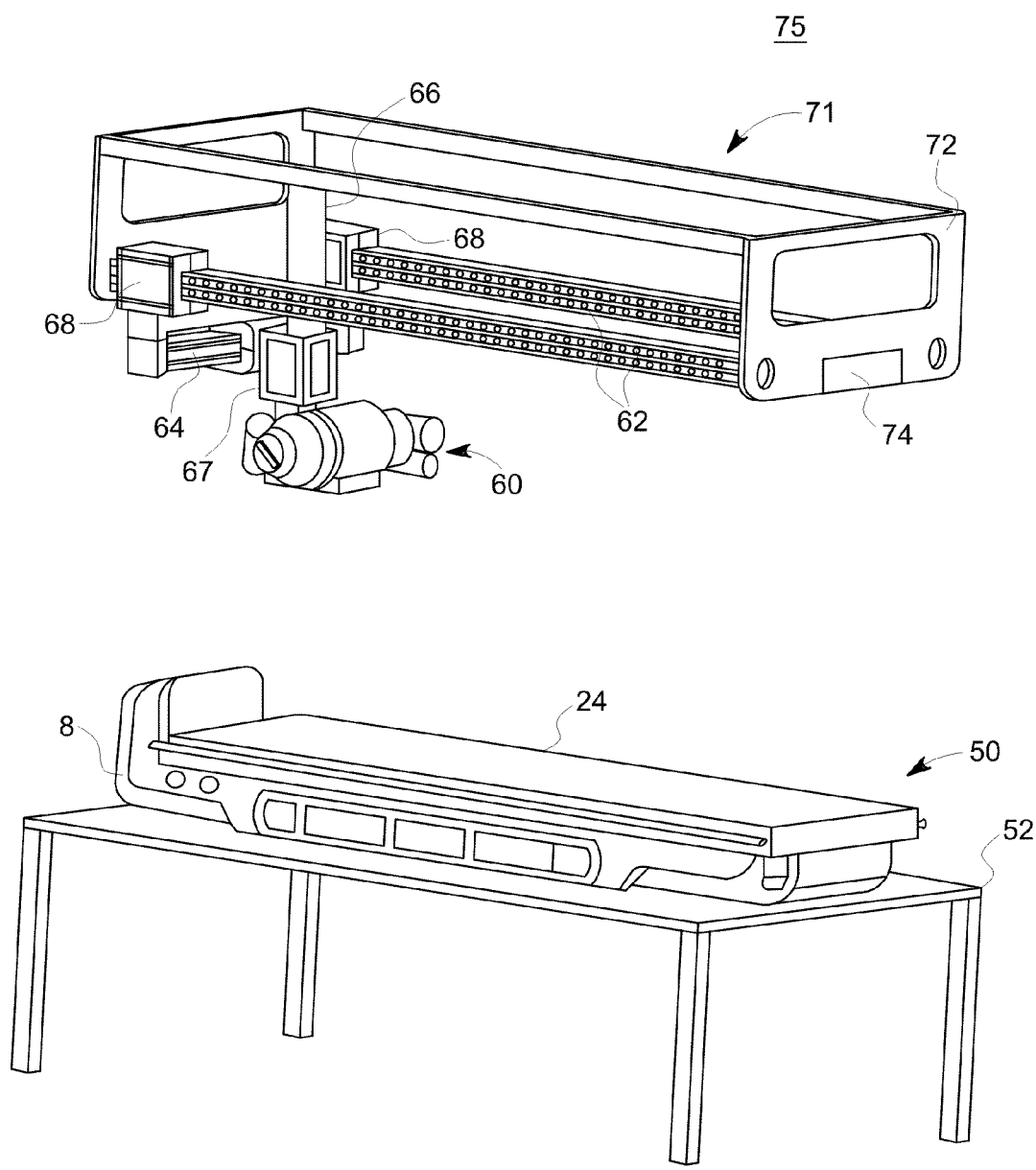

In one embodiment, as described with respect to FIG. 8B, a single X-ray source may be moved on an open gantry to generate X-rays at multiple focal spot locations. The imaging system 75 of FIG. 8 includes a portable litter 50 adapted with a detector for imaging as previously described and a source structure 71. In the illustrated embodiment, the portable litter 50 has been positioned on a portable imaging platform 52. The portable imaging platform 52 may represent a fixed or portable table or stand upon which the portable litter can be positioned. In one embodiment, the portable imaging platform 52 may include an alignment mechanism to align the portable litter 50 in a determined orientation with respect to the source structure 71. Moreover, the portable litter 50 and the portable imaging platform 52 may include complementary communications interfaces which may, for example, provide bidirectional transfer of X-ray acquisition data, detector position and orientation information, or supply power to the portable litter 50. As alluded to, the source structure 71 is configured to generate X-rays from different focal spot locations. In accordance with the illustrated embodiment, a series of X-ray projection acquisitions acquired from two-dimensional tomographic trajectories can be reconstructed to form a three-dimensional image. In one embodiment, the two-dimensional tomographic trajectories are formed from multiple linear trajectories.

The X-ray source 60 may be movably mounted on an open gantry 72. In the illustrated embodiment, the open gantry 72 may include a support structure that is adapted to be mounted above an X-ray detector. In accordance with one embodiment, the X-ray source 60 is adapted to move with respect to the portable litter 50 along the gantry in at least two orthogonal planes. In accordance with the illustrated embodiment of FIG. 8B, the X-ray source 60 is adapted to move with respect to the portable litter 50 along the open gantry 72 in three orthogonal (X,Y,Z) planes as shown.

In the illustrated embodiment, the X-ray source 60 is coupled to a movable member 66 by an articulating joint such that the source 60 may pan (e.g., in the X-Z plane) and tilt (e.g., in the X-Y plane). Additionally, movable member 60 may be telescoping or otherwise extendable in the Y-axis such that the X-ray source 60 may be moved toward or away from the portable litter 50. The movable member 66 may move with respect to a coupling 67. The coupling 67 may in turn be movably coupled to a cross-member 64 which allows the X-ray source 60 to move in the direction of the X-axis as shown. Additionally, the cross-member 64 (and by extension, the X-ray source 60) may further be movably coupled to one or more source supports 62 to allow the X-ray source 60 to move in the direction of the Z-axis as shown. In one embodiment, the cross-member 64 may be coupled to the one or more supports 62 by one or more couplings 68.

In one embodiment, movement of the X-ray source 60 upon the open gantry 72 may be controlled by a controller 74. The controller 74 may be integrated as part of the source structure 71 (as shown) or it may be remotely located and communicatively coupled to the source structure 71 either by wire or wirelessly. The controller 74 may include one or more general or special purpose processors equipped with instructions or code, which when executed cause the X-ray source 60 to be moved in one or more orthogonal planes and for the X-ray source 60 to pan or tilt depending upon the source angle desired. Furthermore, the controller 74 may be configured to cause the X-ray source 60 to emit X-rays in response to a triggering event. The triggering event may be representative of an operator initiating an acquisition or series of acquisitions. In one embodiment, the controller 74 is configured to generate a plurality of individual X-ray acquisitions arranged in a grid-like pattern above the portable litter 50. The grid pattern may be defined as a first number M of acquisitions made along the Z-axis of the open gantry 72, and a second number N of acquisitions made along the X-axis of the open gantry 72. The pattern of individual X-ray acquisitions may be chosen so as to maximize depth resolution while minimizing patient scatter. In one embodiment, the controller 74 may include a preprogrammed acquisition routine which may be automatically executed upon the commencement of the imaging process. In particular, the controller 74 may include a series of pre-programmed gantry coordinates at which point X-ray acquisitions may be made. For example, if a subject with leg trauma is positioned on the portable litter 50 under the source structure 71, an operator may indicate to the controller 74 that an acquisition routine specific to a leg-scan should be run. This routine may include pre-programmed instructions and/or coordinates that would define the range of movement and acquisitions that the X-ray source 60 should follow.

The controller may also be communicatively coupled to the one or more detectors of the portable litter 50 to indicate to the detector when to operate in a receive mode. Read-out circuitry coupled to the digital detector within the portable litter 50 may be synchronized with the X-ray source to output the X-ray exposure state of the picture elements within the detector. This exposure information may in turn be communicated to a local or remotely coupled image processor to reconstruct a tomographic image from the series of two-dimensional acquisitions from the source structure 71. In one embodiment, the imaging system 75 may be used to produce real time fluoroscopic images. "Fluoroscopic images" as used herein refers to the continuous acquisition of a sequence of X-ray images over time. For example, fluoroscopic images may be acquired at a rate of at least 15 frames per second. These real time fluoroscopic images can be used for diagnosing the existence of a problem, and determining an appropriate interventional procedure. Furthermore, fluoroscopic image sequences can enable minimally invasive interventional procedures. Moreover fluoroscopic images may also be fused with tomographic data sets.

Figure 9:
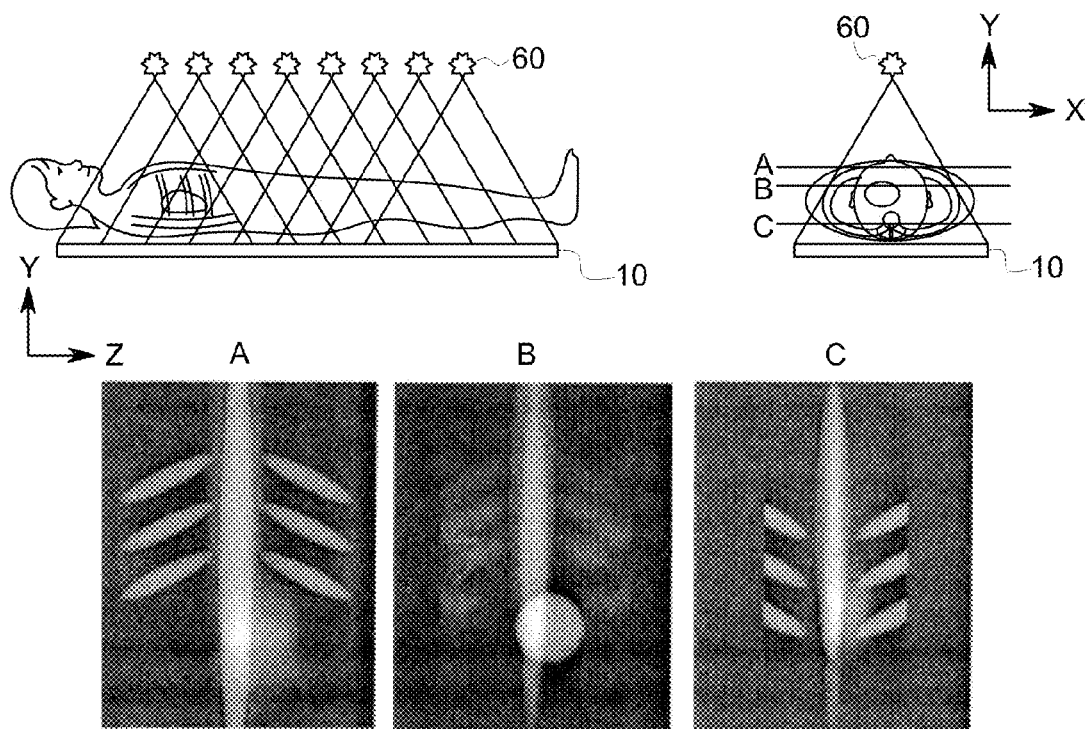
FIG. 9 and FIG. 10 illustrate tomographic reconstructions of synthetic data sets obtained by imaging an X-ray phantom according to various embodiments of the invention.
Figure 10:
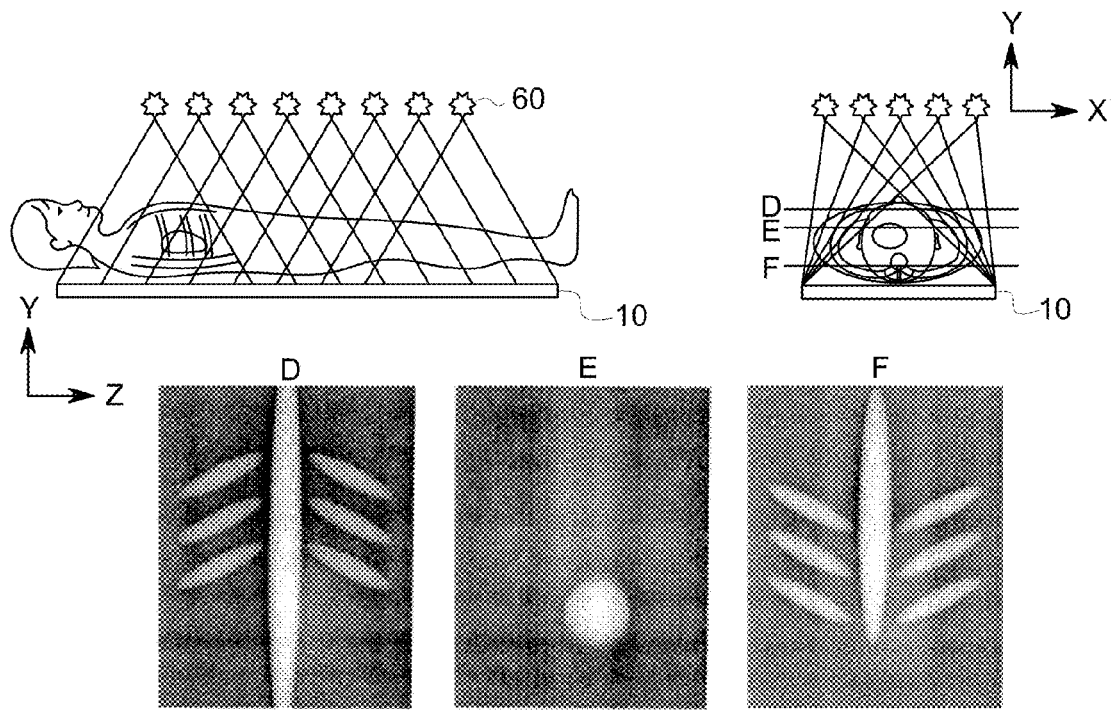

FIG. 9 and FIG. 10 illustrate tomographic reconstructions of synthetic data sets obtained by imaging an X-ray phantom according to various embodiments of the invention. The synthetic phantom contains geometric objects meant to represent various elements of human chest anatomy at various depths.

In FIG. 9, a series of images (A, B, C) reconstructed from a linear tomographic trajectory along the longitudinal axis (Z-axis) are shown. When the X-ray source 60 is moved in this fashion, a series of images can be acquired by the detector which can then be reconstructed into a three-dimensional data set that can be viewed as a sequence of two-dimensional images. Any of a wide variety of image reconstruction techniques known or yet to be developed may be utilized in the reconstruction process. Each reconstructed image is in focus at a specific depth within the subject. Each of the images (A, B, C) in FIG. 9 represents a single slice through the reconstructed three-dimensional tomographic volume as indicated. However, while reconstructed data is three-dimensional in nature, the depth information is limited and may be subject to reconstruction artifacts. These artifacts can be seen in the images as blurring induced from high contrast out of plane objects.

In FIG. 10, a series of images (D, E, F) reconstructed from a two-dimensional tomographic trajectory along the longitudinal axis (Z-axis) and the lateral axis (X-axis) of the same X-ray phantom of FIG. 9 are shown. As can be seen, the image artifacts caused by out of plane structures in images A, B and C are substantially reduced as compared to images D, E and F, respectively.

In order to achieve good image quality, the relative position of source and detector during image acquisition needs to be at least partially known. In one embodiment, this may be achieved through hardware based positioning of detector and/or X-ray source points in locations that are well-known in advance (e.g., source and detector supports may be "secured into place" in some common mechanical reference frame or alignment mechanism). In another embodiment, a partial measurement of the distances and orientations of X-ray source points (focal spot locations) may be performed. For example, both source assembly and detector assembly may be positioned such that they are each in a horizontal position. This can be done with the aid of a leveling device. An orientation sensor (e.g., a compass) may be used to determine the horizontal orientation of the source assembly, and the detector assembly. Although in this scenario the relative position of detector and source is only partially known (since their distance in height, as well as any lateral offset within the horizontal plane is not determined), an excellent 3D image quality can be achieved in the reconstructed dataset, as long as the relative position of source points (focal spots) within the source assembly is accurately known. Alternative embodiments may utilize different sensors known in the art in order to determine the relative position of source assembly and detector assembly. In yet another embodiment, information about the relative position of detector and source points may be extracted from the acquired images themselves, e.g., using markers that are present in the imaged volume. The markers may be natural or synthetic and may be anatomical markers such as bones present in the imaged anatomy. From the markers that can then be found in the acquired images, information about the imaging geometry may be extracted. For example, some methods that use this type of information are described in U.S. patent application Ser. No. 11/701,760 "METHOD AND SYSTEM FOR THREE-DIMENSIONAL IMAGING IN A NON-CALIBRATED GEOMETRY", filed on Feb. 2, 2007. Note that some of these markers may be embedded in the litter itself, and may consist of spheres, wires, or other shapes in different configurations. Also, partially radiolucent structures may be used, thereby minimizing the potential problem of occlusion caused by these markers. Hybrid methods may also be used, where aspects of one or more of the previously described approaches are combined to determine the imaging geometry. For example, the source assembly may be mounted within a mechanical framework that provides a known horizontal position of the source points (or a position that is parallel to the detector plane), while the remaining imaging geometry information is extracted from the location of markers embedded in the litter in the acquired images.

Figure 11:
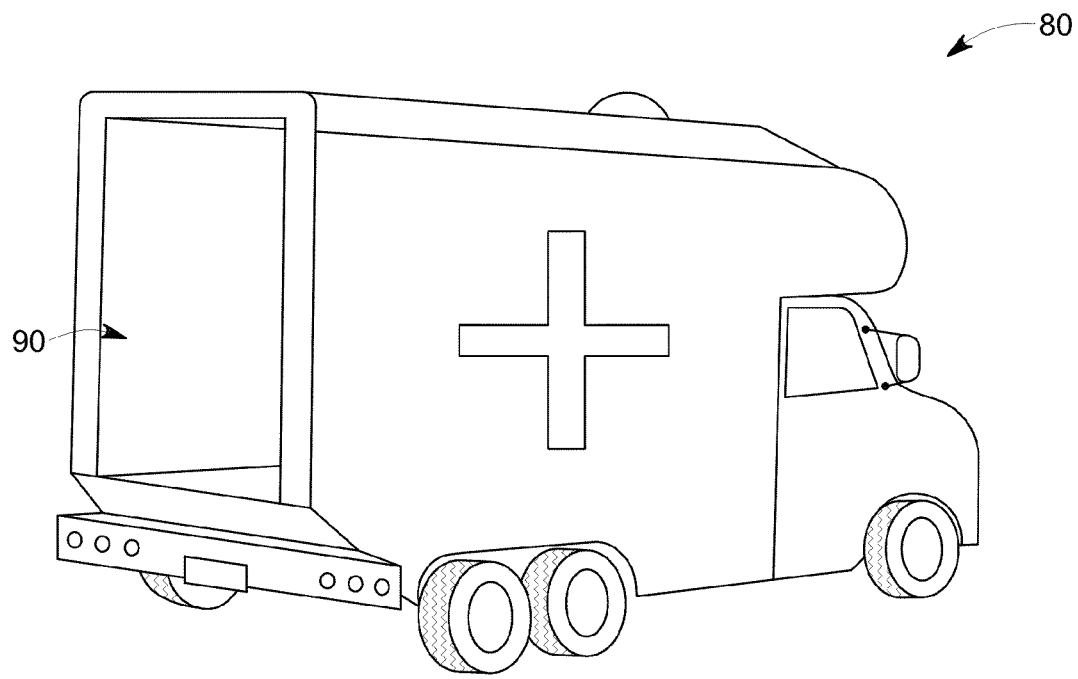
FIG. 11 illustrates a patient transport adapted for imaging in accordance with one embodiment of the invention.

FIG. 11 illustrates a patient transport adapted for imaging in accordance with one embodiment of the invention. In the illustrated embodiment, a patient transport 80 is illustrated in the form of a motorized vehicle adapted for imaging. The patient transport 80 may be configured to provide portable imaging capabilities to remote areas or locations that might not otherwise have tomographic imaging equipment available. Additionally, the patient transport 80 may be equipped with a high-bandwidth transmitter to allow X-ray acquisition data to be transmitted to a remote base station where the data can be analyzed and/or reconstructed. In a specific application, the patient transport 80 may represent a military ambulance adapted to perform remote tomographic imaging in accordance with teachings herein.

In an embodiment where the patient transport 80 represents a motorized vehicle as in FIG. 11, the vehicle may include an internal combustion engine, an electric motor, or a hybrid propulsion system. However, a patient transport need not include a propulsion system and may be operated by a local or remote driver/operator. In one embodiment, the patient transport 80 may include a cab, and a cargo area 90 attached to the cab.

Figure 12:
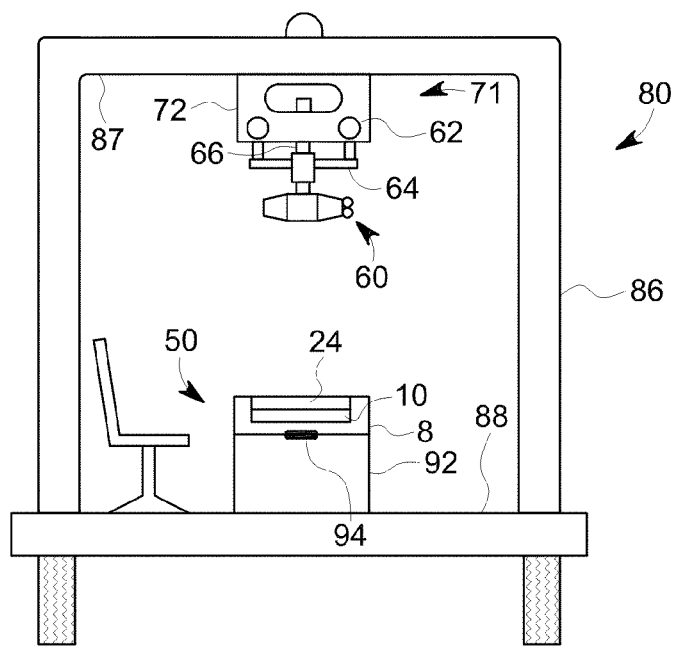
FIG. 12 illustrates a rear view of the patient transport 80 of FIG. 11, in accordance with one embodiment.

FIG. 12 illustrates a rear view of the patient transport 80 of FIG. 11, in accordance with one embodiment. As shown, the cargo area 90 is defined by a wall 86, a ceiling 87 and a floor 88. In one embodiment, the wall 86, the ceiling 87 and the floor 88 may include X-ray shielding to prevent X-rays from exiting the cargo area 90. Within the cargo area 90, a portable imaging system including a source structure 71 and a portable litter 50 (e.g., as described with respect to FIG. 8B) is provided. The source structure 71 includes an open gantry arrangement 72 fixedly coupled to the ceiling 87 of the cargo area 90, and an X-ray source 60 for generating X-ray signals movably coupled to the open gantry arrangement 72. Additionally, the cargo area 90 includes a support structure 92 coupled to the floor 88 of the cargo area 90 and a portable litter 50 removably coupled to the support structure 92. As previously described, the portable litter 50 may include a structural housing 8 and a digital detector 10 coupled to the structural housing to detect X-ray signals from the source. The portable litter 50 may further include a radiolucent surface 24 over the digital detector 10 and upon which a subject to be imaged may be laid. In one embodiment, the portable litter 50 may be releasably coupled to the support structure 92. For example, an injured subject lying on the portable litter may be placed on, and secured to the support structure 92 for imaging without the need to transfer the subject to a separate table, thereby preventing additional aggravation to the injury. In one embodiment, the support structure 92 may include a communications interface configured for mating with a complementary communications interface on the portable litter 50 for transfer of X-ray acquisition data, detector position and orientation information, supply power or a combination thereof. The communications port 94 may further include a power coupling to provide the portable litter with operating current while within the patient transport 80.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A portable litter for imaging comprising:
 a structural housing;
 a digital detector positioned in the structural housing to detect X-ray signals corresponding to a region of interest to be imaged, wherein the digital detector comprises an image processor and a plurality of digital detector panels, wherein the digital detector panels are spaced apart and selectively coupled to the image processor based upon a location of the region of interest;
 a radiolucent surface disposed above the digital detector; and
 an energy storage device coupled to the digital detector.

2. The portable litter of claim 1, further comprising readout circuitry coupled to the digital detector to determine an X-ray exposure state of a plurality of picture elements within the detector.

3. The portable litter of claim 2, further comprising a transmitter to transmit signals representative of the X-ray exposure state of the picture elements to a remote analysis node.

4. The portable litter of claim 2, further comprising a data port positioned on an underside of the structural housing opposite the radiolucent surface and adapted to be mated with a complementary data port for transmitting the X-ray exposure state of the picture elements.

5. The portable litter of claim 1, wherein the digital detector is slidably coupled to the structural housing and is movable in at least one of a lateral or longitudinal direction.

6. The portable litter of claim 1, further comprising at least two supports coupled to the structural housing to slidably support the digital detector.

7. The portable litter of claim 1, wherein the portable litter further comprises at least one monitoring device for monitoring at least one physiological measurement of a patient.

8. An imaging system comprising:
 an open gantry;
 a portable litter including a structural housing and a digital detector positioned in the structural housing to detect X-ray signals corresponding to a region of interest to be imaged;
 at least one X-ray source for generating the X-ray signals, the at least one X-ray source positioned above the portable litter on the open gantry and configured to generate X-rays from different focal spot locations; and
 a fixed support structure positioned below the open gantry to receive and support the portable litter, wherein the support structure comprises a data port configured to be mated with a complementary data port on the portable litter to receive data representing an X-ray exposure state of a plurality of picture elements in the detector.

9. The imaging system of claim 8, wherein the at least one X-ray source comprises at least one of a distributed source and a movable source.

10. The imaging system of claim 8, wherein the imaging system is contained within a motorized vehicle.

11. The imaging system of claim 8, wherein the at least one X-ray source is adapted to move on the open gantry.

12. The imaging system of claim 11, wherein the at least one X-ray source is adapted to move in at least a grid, raster or arc pattern.

13. The imaging system of claim 8, wherein the at least one X-ray source comprises a distributed X-ray source configured to generate X-rays from different focal spot locations.

14. The imaging system of claim 13, wherein the distributed X-ray source is moved with respect to the open gantry.

15. The imaging system of claim 13, wherein the portable litter is moved with respect to at least one X-ray source.

16. The imaging system of claim 8, wherein the digital detector is slidably coupled to the structural housing and is movable in at least one of a lateral or longitudinal direction.

17. The imaging system of claim 8, wherein the portable litter further comprises at least two supports coupled to the structural housing to slidably support the digital detector.

18. The imaging system of claim 8, wherein the digital detector comprises an image processor and a plurality of digital detector panels, wherein the digital detector panels are spaced apart and selectively coupled to the image processor based upon a location of the region of interest.

19. The imaging system of claim 8, wherein the at least one X-ray source is adapted to move on the open gantry in at least three-orthogonal planes.

20. The imaging system of claim 8, wherein the portable litter further comprises at least one monitoring device for monitoring at least one physiological measurement of a patent.

21. The imaging system of claim 8, further comprising an alignment mechanism to control the relative positions of the digital detector and the at least one X-ray source.

22. The imaging system of claim 21, wherein the alignment mechanism aligns the digital detector and the at least one X-ray source in a determined horizontal position and a determined horizontal orientation.

23. The imaging system of claim 8, comprising means to obtain information about the alignment of the digital detector and the at least one X-ray source.

24. The imaging system of claim 23, wherein information about the alignment of the digital detector and the at least one X-ray source is extracted from acquired images.

25. A patient transport for imaging comprising;
a cab; and
a cargo area attached to the cab and having a ceiling and a floor, the cargo area comprising:
an open gantry arrangement fixedly coupled to the ceiling of the cargo area;
an X-ray source for generating X-ray signals coupled to the open gantry arrangement;
a support structure coupled to the floor of the cargo area; and
a portable litter removably coupled to the support structure, the portable litter including a structural housing and a digital detector coupled to the structural housing to detect X-ray signals from the source, wherein the support structure comprises a data port configured to be mated with a complementary data port on the portable litter to receive data representing an X-ray exposure state of a plurality of picture elements in the digital detector.

26. The patient transport of claim 25, wherein the cargo area comprises X-ray shielding.

27. The patient transport of claim 26, wherein the X-ray shielding is integrated within the cargo area.

* * * * *